United States Patent [19]

Kling

[11] 4,323,065
[45] Apr. 6, 1982

[54] ATTACHABLE CONNECTOR FOR CATHETER

[75] Inventor: John E. Kling, Dallas, Tex.

[73] Assignee: Baxter Travenol Laboratories, Inc., Deerfield, Ill.

[21] Appl. No.: 113,099

[22] Filed: Jan. 17, 1980

[51] Int. Cl.³ .............................................. A61M 5/00
[52] U.S. Cl. ............................. 128/214 R; 128/247; 285/322; 285/DIG. 22
[58] Field of Search ..................... 128/214, 214.4, 247, 128/348, 221, 334 C; 285/322, 323, 315, 319, 423, 243, DIG. 22; 403/289

[56] References Cited

U.S. PATENT DOCUMENTS

| 767,893 | 8/1904 | Jewell | 285/243 |
| 1,469,493 | 10/1923 | Brown | 294/86.24 |
| 3,413,021 | 11/1968 | Potts | 285/319 |
| 3,484,121 | 12/1969 | Quinton | 285/242 |
| 3,752,510 | 8/1973 | Windischman | 285/334.4 |
| 3,898,993 | 8/1975 | Taniguchi | 128/349 R |
| 3,977,403 | 8/1976 | Patel | 128/221 |
| 3,997,195 | 12/1976 | Bartholomew | 285/423 X |
| 4,006,744 | 2/1977 | Steer | 128/214 R |
| 4,013,310 | 3/1977 | Dye | 285/322 X |

Primary Examiner—Stephen C. Pellegrino
Attorney, Agent, or Firm—Richards, Harris & Medlock

[57] ABSTRACT

A connector (10) for attachment to a catheter (14) includes a fitting (16) with a plurality of resilient fingers (22) extending from one end thereof in surrounding relationship with an axial bore (18). A tapered bore (20) is provided at the opposite end of the fitting (16) for receiving the tip of a syringe (12). A slidable ring (34) is mounted on the fingers (22) for irreversible movement from an unlocked position to a locked position wherein the connector (10) and catheter (14) are secured together. In the preferred embodiment, a protective boot (40) is mounted on the locking ring (34) to provide stress relief between the catheter (14) and the connector (10).

7 Claims, 5 Drawing Figures

U.S. Patent     Apr. 6, 1982     4,323,065
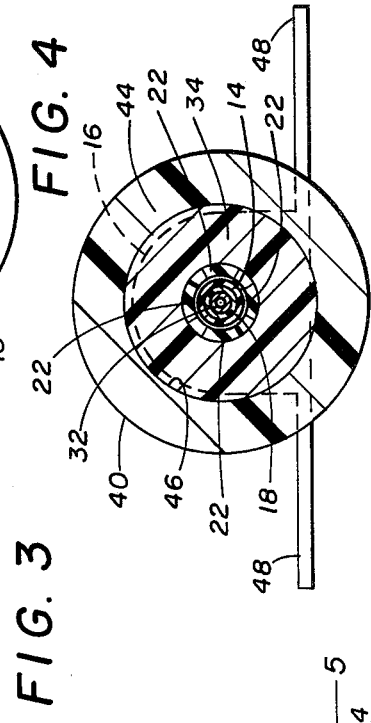
FIG. 1
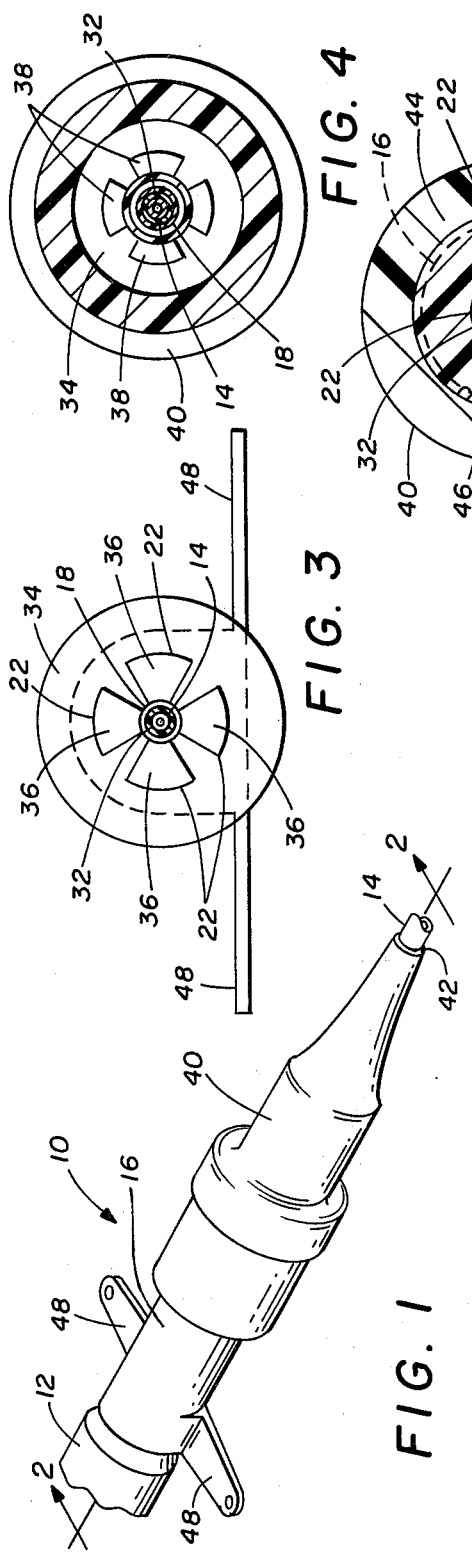
FIG. 3
FIG. 4
FIG. 5
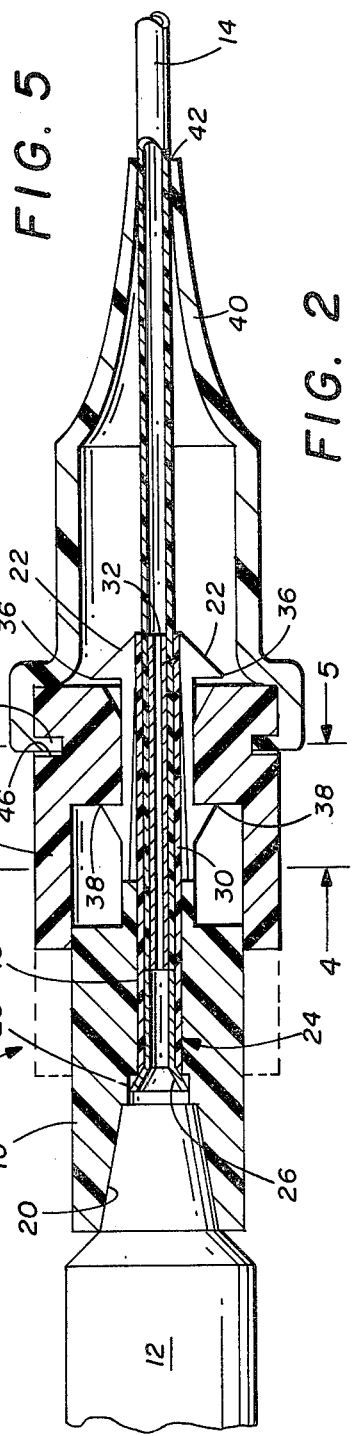
FIG. 2

4,323,065

ATTACHABLE CONNECTOR FOR CATHETER

TECHNICAL FIELD

The present invention relates in general to a fluid coupling device. More particularly, this invention concerns a connector for interconnecting a section of tubing, such as a catheter, in fluid communication with another object.

BACKGROUND ART

Various medical procedures require connection of an infusion device to the end of a catheter. During some anesthesia procedures, for example, a catheter is positioned in the body of a patient, after which anesthetic fluid is injected through the catheter by means of a syringe connected to the proximal end of the catheter. Accordingly, a connector must be provided for attaching a syringe or other infusion device to the proximal end of the catheter.

Attachment of a connector to a catheter or section of cannula tubing, however, involves several difficulties. By reason of their use, catheters are formed of soft, pliable materials and are not of particularly rugged construction. Catheters are thus susceptible to damage or collapse, thereby complicating the difficulty of achieving a secure fluid-tight seal between the catheter and connector without damaging the catheter.

Several types of connection devices have been developed for use with catheters. The devices shown in U.S. Pat. Nos. 3,752,510 to Windischman, et al., and 3,977,403 to Patel are representative of the prior art. A widely used connector at the present time is the Thoey-Borst connector, which is a three-piece device operated by compression of an O-ring between two threaded members.

The catheter connectors available heretofore, however, suffer from various disadvantages, including lack of sufficient stress relief at the junction of the catheter and connector to prevent damage to the catheter, and the troublesome tendency to become disconnected. A need has thus arisen for a new and improved connection device for use with catheters.

DISCLOSURE OF THE INVENTION

The present invention comprises a fluid coupling device which overcomes the foregoing and other problems associated with the prior art. In accordance with the invention, there is provided a connector for attachment to the end of a length of flexible tubing to facilitate fluid coupling of another object thereto. The connector herein provides a good fluid-tight seal around the end of the tubing and features one-way irreversible action to prevent disconnection of the connector from the tubing. The connector herein also provides reinforcement and therefore stress relief at the junction between the connector and tubing to reduce potential damage to the flexible tubing.

More specifically, the present invention comprises a connector adapted especially for use with a catheter or section of cannula tubing characterized by flexible, pliable construction. The connector includes a hub having a passageway extending therethrough between a rearward female luer adapter for receiving an infusion device and forwardly extending split fingers within which an end of the catheter is received. A sliding ring is mounted on the fingers for one-way irreversible movement from an unlocked position to a locked position in which the catheter is clamped securely within the split fingers. Barbs on the fingers define the locked position for the sliding ring. In the preferred embodiment, a flexible boot is mounted on the sliding ring to provide stress relief between the catheter and connector especially when the ring is moved to the locked position.

BRIEF DESCRIPTION OF DRAWINGS

A more complete understanding of the invention can be had by reference to the following Detailed Description in conjunction with the accompanying Drawings, wherein:

FIG. 1 is a perspective view of an infusion device coupled to a catheter by means of a connector constructed in accordance with the invention;

FIG. 2 is an enlarged sectional view taken along lines 2—2 of FIG. 3;

FIG. 3 is an end view of the invention with the protective boot removed;

FIG. 4 is a sectional view taken along lines 4—4 of FIG. 2 in the direction of the arrows; and FIG. 5 is a sectional view taken along lines 5—5 of FIG. 2 in the direction of the arrows.

DETAILED DESCRIPTION

In the Drawings, like reference numerals designate like or corresponding elements throughout the views.

Referring now to FIG. 1, there is shown a connection device or connector 10 of the present invention. Connector 10 is utilized to connect an infusion device or syringe 12 to a section of cannula tubing or a catheter 14 extending inside a patient. As will be more fully explained hereinafter, connector 10 provides a secure fluid-tight seal with catheter 14 by means of an irreversible locking mechanism, and provides stress relief at the junction between the catheter and the connector to avoid damage to the catheter.

Although connector 10 is particularly adapted for use in medical procedures involving catheters, it will be appreciated by those skilled in the art that the present invention can also be utilized in other fluid coupling applications wherein it is desirable to connect a section of flexible tubing to another object.

The structural details of connector 10 are shown in FIGS. 2-5. Connector 10 includes a hub 16 having a longitudinal bore 18 therein. Hub 16 can be formed of plastic or other suitable material. The proximal end of hub 16 includes a tapered bore 20 which, in accordance with the preferred construction, comprises a female luer taper as is well known in the prior art. The distal end of hub 16 includes a plurality of resilient fingers 22 attached thereto around the end of bore 18. For purposes of illustration, four fingers 22 are shown; however, any suitable number of fingers can be utilized. Hub 16 and fingers 22 are preferably of integral construction as illustrated.

In the preferred construction of connector 10, an insert 24 is disposed within bore 18. Insert 24 includes a rigid collar 26 that is press fitted into a concentric counter bore 28 provided at the inside end of tapered bore 20. Collar 26 extends from counter bore 28 forwardly inside passage 18. A flexible liner or inner sleeve 30 surrounds a portion of collar 26 and extends therefrom through bore 18 and the remainder of hub 16 to the end of fingers 22.

Catheter 14 is thus received within sleeve 30 and bore 18 as defined by fingers 22 at the distal end of hub 16. Catheter 14 preferably includes a rigid inner sleeve 32 which is positioned within fingers 22 when the catheter is seated inside connector 10. When inserted into connector 10, catheter 14 is positioned between rigid sleeve 32 and flexible sleeve 30 between fingers 22. While the use of inner sleeve 32 is desirable with catheters and other types of flexible tubing, it will be appreciated that connector 10 can be utilized with tubing or relatively less flexibility without such a sleeve.

A sliding ring 34 is mounted on fingers 22. Ring 34, which is circular and may include a rearward skirt surrounding a portion of hub 16, may be constructed of plastic or other suitable material. Ring 34 is mounted for one-way, irreversible movement from an unlocked position, which is shown in phantom lines in FIG. 2, to a locked position as shown in full lines. Provision of a one-way irreversible sliding ring 34 which locks in place comprises a significant feature of the present invention.

Ring 34 is secured in the locked position by pairs of barbs 36 and 38 provided on fingers 22. Barbs 36 prevent ring 34 from leaving the end of fingers 22, while barbs 38 prevent the ring from returning to the unlocked position. The surfaces of fingers 22 between barbs 36 and 38 define a slightly conical or inclined surface so that the fingers of body member 16 will be forced inwardly when ring 34 is pushed forward. The angle of inclination between barbs 36 and 38 can be, for example, about 2-3 degrees. During assembly of connector 10, when no catheter 14 is positioned therein, resilient fingers 22 collapse inward sufficiently to allow ring 34 to pass over barbs 36 and 38 to the unlocked position.

In accordance with the preferred construction, connector 10 includes a protective boot 40 mounted on ring 34. Boot 40 is generally funnel-shaped and can be formed from rubber or other suitable material. A central opening 42 is provided at the end of boot 40 for receiving catheter 14. As is best shown in FIG. 2, boot 40 includes a lip 44 for receipt by a groove 46 of ring 34 to secure the boot to the locking ring. When ring 34 is pushed forward to the locked position, it will be appreciated that protective boot 40 advances therewith over catheter 14 to provide reinforcement and stress relief at the junction between the catheter and connector 10.

If desired, connector 10 can be provided with additional features to facilitate manipulation thereof. A pair of eyelets 48 can be molded into body member 16 so that connector 10 can be sutured in place. A conventional luer lock (not shown) can also be molded into body member 16 so that syringe 12 can be releasably engaged with connector 10. For example, such a luer lock may take the form of flange 33 of the catheter plug assembly shown in U.S. Pat. No. 4,137,916, the disclosure of which is incorporated herein by reference.

From the foregoing, it will be apparent that the present invention comprises a catheter connector having several advantages over the prior art. One significant feature of the invention is the use of an irreversible locking ring for securing the connector to the catheter with a fluid-tight seal, while preventing disconnection from the catheter. Another feature is the provision of a protective boot mounted on the locking ring for stress relief at the junction between the catheter and the connector. Other advantages will be apparent to those skilled in the art.

Although a particular embodiment of the invention has been illustrated in the accompanying Drawing and described in the foregoing Detailed Description, it will be understood that the invention is not limited to the embodiment disclosed, but is intended to embrace any equivalents, alternatives, and/or modifications of elements as fall within the spirit and scope of the invention.

I claim:

1. A connector for attachment to a section of tubing, such as a catheter or the like, comprising:
    a hub having a distal end and a proximal end, and an axial bore extending therethrough sized for receipt of the tubing;
    said hub including a tapered chamber at the proximal end thereof in fluid communication with the bore;
    a plurality of resilient fingers extending outwardly from the distal end of said hub in surrounding relationship with the bore;
    a slidable ring mounted for movement along said fingers from an unlocked position to a locked position wherein the connector and the tubing are secured together in fluid communication; and
    said fingers each including a pair of oppositely facing barbs for retaining said ring in the locked position to prevent disconnection of the connector from the tubing.

2. The connector of claim 1, further including hollow insert means extending through the bore of said hub, said insert means comprising:
    a rigid collar connected adjacent to the proximal end of the bore in said hub; and
    a section of tubing extending from the collar outwardly between said resilient finger means.

3. The connector of claim 1, further including:
    resilient boot means mounted on said slidable ring means for providing stress relief at the junction between the tubing and connector.

4. The connector of claim 1, further including:
    a pair of eyelets mounted on opposite sides of said hub.

5. A connector for coupling an infusion device to the end of a catheter, comprising:
    a hub having a distal end and a proximal end, and an axial bore extending therethrough sized for receipt of the catheter;
    the proximal end of said hub including a tapered chamber in fluid communication with the bore for receiving the infusion device;
    a plurality of resilient fingers extending outwardly from the distal end of said hub in surrounding relationship with the bore;
    a slidable ring mounted for movement along said fingers from an unlocked position to a locked position wherein the connector and the catheter are secured together in fluid communication;
    said fingers each including a pair of oppositely facing barbs for retaining said ring in the locked position to prevent disconnection of the connector from the catheter; and
    a resilient boot mounted on said slidable ring for providing stress relief at the junction between the connector and catheter.

6. A connector for attachment to the end of a section of tubing, which comprises:
    a hub having a distal end and a proximal end, and an axial bore extending therethrough between the ends of said hub;

the distal end of the bore in said hub being dimensioned for receipt of the tubing;

resilient finger means extending outwardly from the distal end of said hub in surrounding relationship with the bore therein;

slidable ring means mounted on said finger means for movement from an unlocked position adjacent said hub to a locked position adjacent the end of said finger means in which the connector and the tubing are secured together in fluid communication;

locking means associated with said slidable ring means and finger means for irreversibly locking the ring means in the locked position engaging the finger means to secure the connector and tubing together; and resilient boot means mounted on said slidable ring means adapted to providing stress relief at the junction between the tubing and connector by surrounding the tubing adjacent the connector.

7. A connector for attachment to the end of a section of tubing, which comprises:

a hub having a distal end and a proximal end, and an axial bore extending therethrough between the ends of said hub;

the distal end of the bore in said hub being dimensioned for receipt of the tubing;

resilient finger means extending outwardly from the distal end of said hub in surrounding relationship with the bore therein;

slidable ring means mounted on said finger means for movement from an unlocked position adjacent said hub to a locked position adjacent the end of said finger means in which the connector and the tubing are secured together in fluid communication;

locking means associated with said slidable ring means and finger means for irreversibly locking the ring means in the locked position engaging the finger means to secure the connector and tubing together; and hollow insert means extending through the bore of said hub, including a rigid collar connected adjacent to the proximal end of the bore in said hub and a section of tubing extending from the collar outwardly within said resilient finger means.

* * * * *